(12) United States Patent
Stone

(10) Patent No.: US 7,828,751 B2
(45) Date of Patent: Nov. 9, 2010

(54) METHOD AND APPARATUS FOR RETAINING A FIXATION PIN TO A CANNULA

(75) Inventor: Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 11/745,215

(22) Filed: May 7, 2007

(65) Prior Publication Data

US 2007/0208294 A1 Sep. 6, 2007

Related U.S. Application Data

(63) Continuation-in-part of application No. 10/870,873, filed on Jun. 17, 2004, now Pat. No. 7,217,246.

(51) Int. Cl.
  *A61B 5/00* (2006.01)
  *A61M 25/00* (2006.01)
(52) U.S. Cl. .................................................... 600/585
(58) Field of Classification Search ................ 600/585, 600/184, 201; 604/523, 533–535, 540, 524, 604/526, 528, 23, 30, 103, 117, 158, 175, 604/236, 247, 264, 102.01, 167.06, 96.01, 604/103.04, 164.03, 165.02; 156/173, 175, 156/86, 294; 606/191, 194; 138/118; 623/1.11, 623/1.35
See application file for complete search history.

(56) References Cited

U.S. PATENT DOCUMENTS

| 4,946,443 | A | 8/1990 | Hauser et al. |
|---|---|---|---|
| 5,267,958 | A | 12/1993 | Buchbinder et al. |
| 5,357,978 | A | 10/1994 | Turk |
| 5,746,720 | A | 5/1998 | Stouder, Jr. |
| 5,879,499 | A | 3/1999 | Corvi |
| 6,007,522 | A | 12/1999 | Agro et al. |
| 6,056,722 | A | 5/2000 | Jayaraman |
| 6,095,990 | A | 8/2000 | Parodi et al. |
| 6,096,009 | A | 8/2000 | Windheuser et al. |
| 6,312,406 | B1 | 11/2001 | Jayaraman |
| 6,346,093 | B1 | 2/2002 | Allman et al. |
| 6,520,951 | B1 | 2/2003 | Carrillo, Jr. et al. |
| 6,699,233 | B2 * | 3/2004 | Slanda et al. ............... 604/533 |
| 6,746,442 | B2 | 6/2004 | Agro et al. |
| 6,926,707 | B2 | 8/2005 | Nash et al. |
| 2002/0029014 | A1 | 3/2002 | Jayaraman |
| 2003/0018340 | A1 | 1/2003 | Branch |
| 2003/0120208 | A1 | 6/2003 | Houser et al. |
| 2005/0165366 | A1 | 7/2005 | Brustad et al. |
| 2006/0074400 | A1 * | 4/2006 | Carrillo et al. ............. 604/523 |
| 2006/0100694 | A1 * | 5/2006 | Globerman ................ 623/1.35 |
| 2008/0009770 | A1 * | 1/2008 | Weber et al. ................ 600/585 |

* cited by examiner

*Primary Examiner*—Max Hindenburg
*Assistant Examiner*—Brian Szmal
(74) *Attorney, Agent, or Firm*—Harness, Dickey

(57) ABSTRACT

A medical device for placement in an anatomy and for use with a guide wire that generally includes a cannula member configured to be inserted into the anatomy. The cannula member has a wall that includes an outer wall surface and an inner wall surface. The inner wall surface defines an inner passage that extends along a longitudinal axis of the medical device. A guide wire holding member is formed in the wall of the cannula member. The guide wire holding member defines a cavity in the wall of the cannula member and an aperture in the inner wall surface in communication with the cavity that can receive the guide wire from the inner passage of the cannula member.

19 Claims, 8 Drawing Sheets

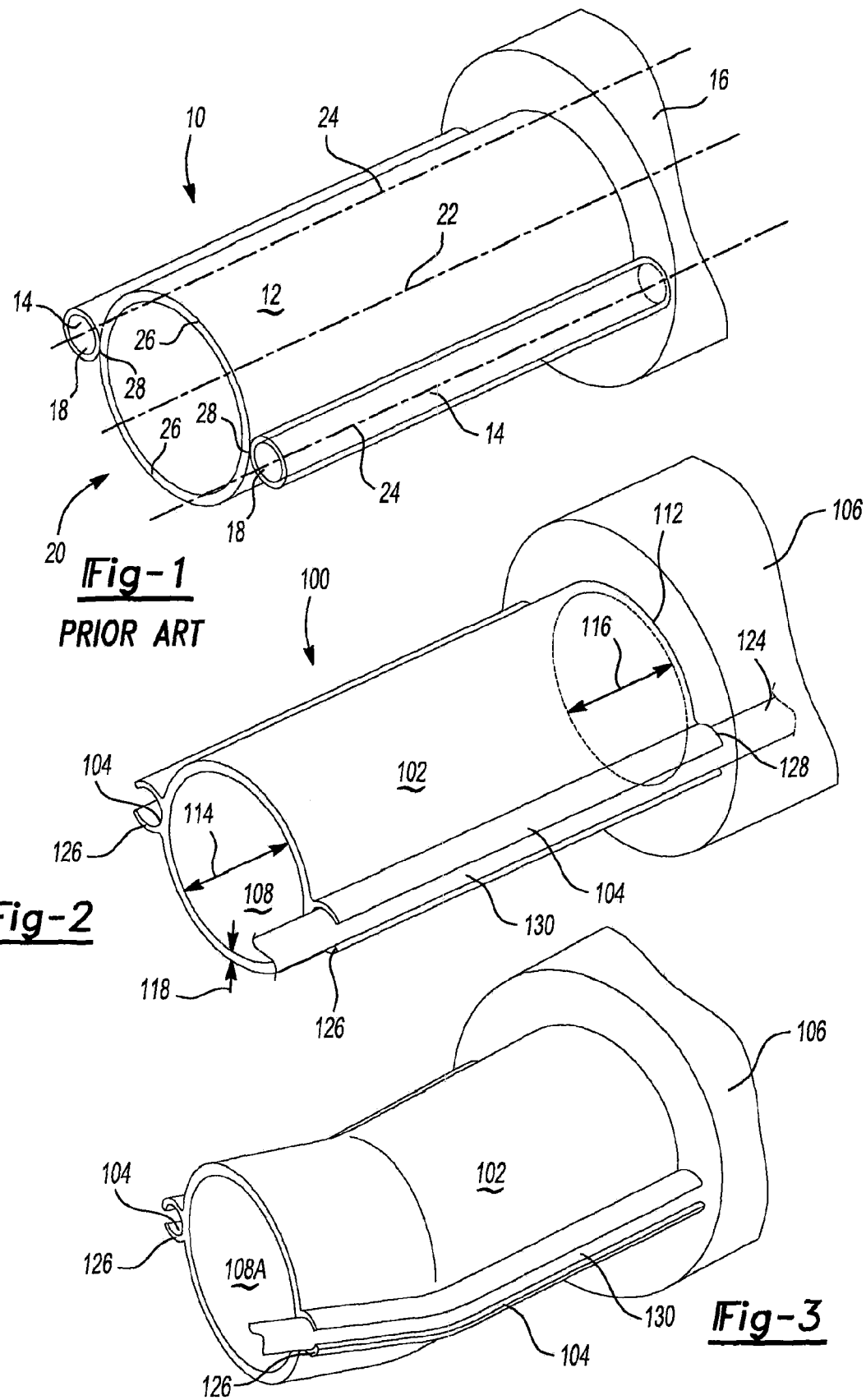

METHOD AND APPARATUS FOR RETAINING A FIXATION PIN TO A CANNULA

CROSS-REFERENCE TO RELATED APPLICATIONS

This application is a continuation-in-part of U.S. patent application Ser. No. 10/870,873 filed on Jun. 17, 2004. The disclosure of the above application is incorporated herein by reference.

FIELD

The present teachings relate to a medical device and more particularly relate to a cannula having guide wire holding members formed in an inner wall surface and accessible from an inner passage of the cannula.

BACKGROUND

With specific reference to FIG. 1, a conventional three-tube cannula is shown and generally indicated by reference numeral 10. The three-tube cannula 10 includes a larger tube 12 to which a pair of smaller tubes 14 are attached. An accessory end 16 is connected to the larger tube 12 and the pair of smaller tubes 14. Guide wires or fixation pins (not shown) can be inserted into a pair of openings 18 and threaded through the pair of smaller tubes 14, so that the three-tube cannula 10 can be supported on the guide wires or the fixation pins. The tip of the three-tube cannula 10 is generally indicated by reference number 20 and is configured to be inserted into a patient through an incision (not shown).

The three-tube cannula 10 is typically made in an injection molding machine (not shown). It will be appreciated that during the forming process the larger tube 12 and the pair of smaller tubes 14 may be formed over tapered pins (not shown but known to one skilled in the art) to ensure the length, diameter and wall thickness of each of the tubes 12, 14. Another consideration is the relative alignment of the larger tube 12 and the pair of smaller tubes 14. More specifically, the larger tube 12 is defined by a center line 22 and the pair of smaller tubes 14 is defined by associated center lines 24. It will be appreciated that as the length of the pins in a typical injection molding machine increase in length, the ability to produce the larger tube 12 in parallel alignment to the pair of smaller tubes 14 becomes more difficult and expensive.

As with any manufacturing process, exact parallel alignment is not always required or attainable. With that said, deviations from absolutely parallel may cause the wall thickness of either the larger tube 12 or the pair of smaller tubes 14 to be too thin when compared to the same cannula manufactured with correct alignment. If a wall thickness 26 is too thin, quality issues arise and the rejection rate from the injection molding machine may become unacceptably high. Moreover, a thickness at a junction indicated by reference numeral 28 between the larger tube 12 and the pair of smaller tubes 14 must not be too thin as the possibility exists of poking the guide wire through one of the smaller tubes 14 into the larger tube 12.

One technique in forming the pair of smaller tubes 14 and/or the primary tube 12 over the pins in the injection molding machine requires gradually flaring one end of the pins, to make it possible to remove the three-tube cannula 10 from the injection molding machine. Flaring is defined as a slight gradual increase of the diameter of a pin at one end when compared to the other end. Because the pins of the injection molding machine are flared or tapered, it necessarily means that one end of the smaller tubes 14 and/or the larger tube 12 will have a larger diameter when compared to an opposite end. This change in diameter necessarily means that the guide wires or fixation pins inserted into the smaller tubes 14 will not be constrained as well when compared to one of the smaller tubes 14 having a constant diameter throughout. When the guide wires are removed or become free from the smaller tubes 14 the guide wires tend to fall away from the three tube cannula 10 as no structure of the cannula retains the guide wires.

SUMMARY

The present teachings generally include a medical device for placement in an anatomy and for use with a guide wire. The medical device generally includes a cannula member configured to be inserted into the anatomy. The cannula member has a wall that includes an outer wall surface and an inner wall surface. The inner wall surface defines an inner passage that extends along a longitudinal axis of the medical device. A guide wire holding member is formed in the wall of the cannula member. The guide wire holding member defines a cavity in the wall of the cannula member and an aperture in the inner wall surface in communication with the cavity that can receive the guide wire from the inner passage of the cannula member.

Further areas of applicability of the present invention will become apparent from the appended claims and detailed description provided hereinafter. It should be understood that the specific examples in the detailed description, while indicating the various embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective View of a conventional three-tube cannula having a larger tube and a pair of smaller tubes attached thereto;

FIG. 2 is a perspective view of a medical device of the present invention showing a cannula member and guide wire holding members connected thereto constructed in accordance with the teachings of the various embodiments of the present invention;

FIG. 3 is similar to FIG. 2 but shows a guide wire in one of the guide wire holding members steering a portion of the cannula member;

DETAILED DESCRIPTION

Figure 4:
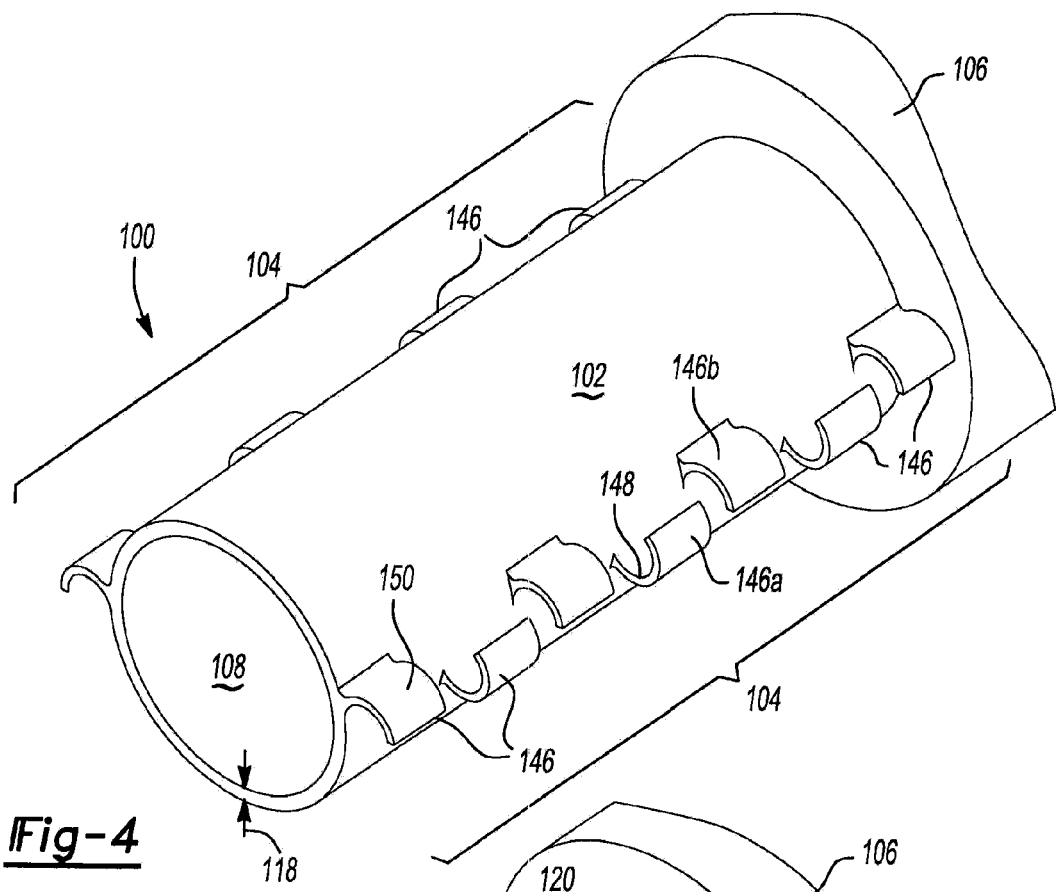
FIG. 4 is similar to FIG. 2 but shows the guide wire holding members configured as a plurality of curled portions.

The following description of the various embodiments is merely exemplary in nature and is in no way intended to limit the invention, its application, or uses.

With reference to FIG. 2, a medical device is generally indicated by reference numeral 100. The medical device 100 includes a main cannula 102 and at least one guide wire holding member 104 attached thereto. It will be appreciated that guide wire holding member 104 can be attached to the main cannula such that the guide wire holding member 104 is connected to the main cannula 102 and affixed with fasteners, bonding chemicals, or other suitable connecting members. The guide wire holder 104 can also be attached to the main cannula 102, such that the guide wire holder 104 is integral to the main cannula 102 and formed of one piece of material. As such, attached or connected thereto is defined as and refers to a one-piece integral construction or a multiple-piece construction attached with suitable fastener members.

Figure 11:
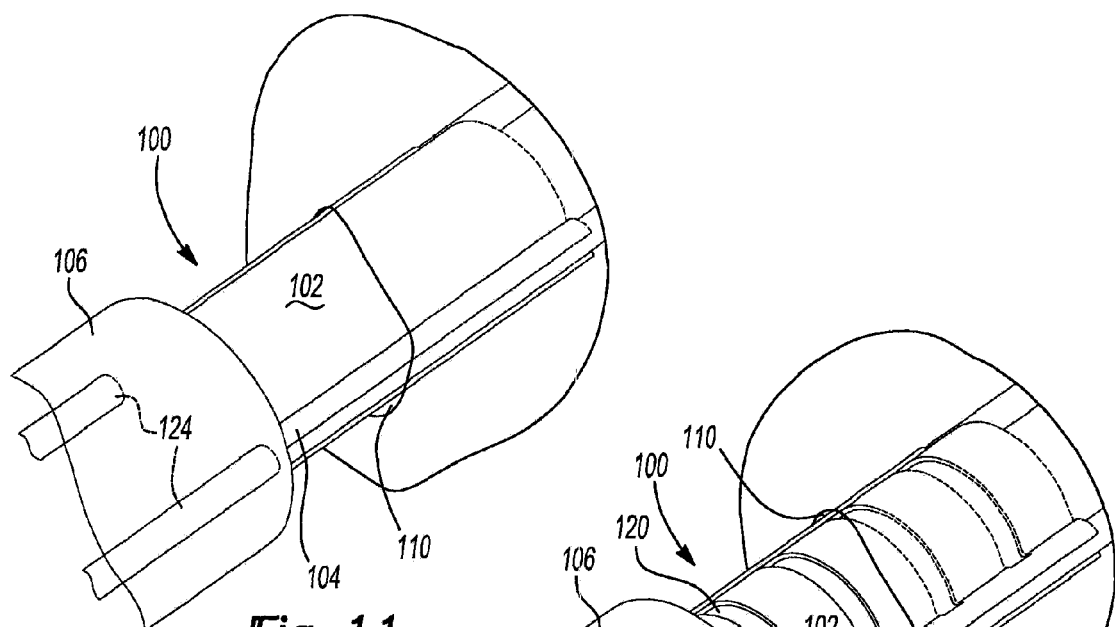
FIG. 11 is a partial perspective view of the medical device of FIG. 2 partially inserted into an incision and placed over a pair of guide wires.
Figure 12:
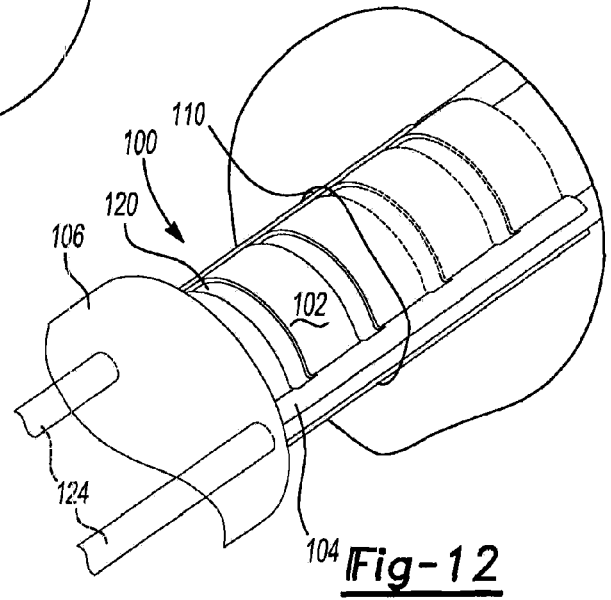
FIG. 12 is a partial perspective view of the medical device of FIG. 5 partially inserted into the incision and placed over a pair of guide wires.
Figure 13:
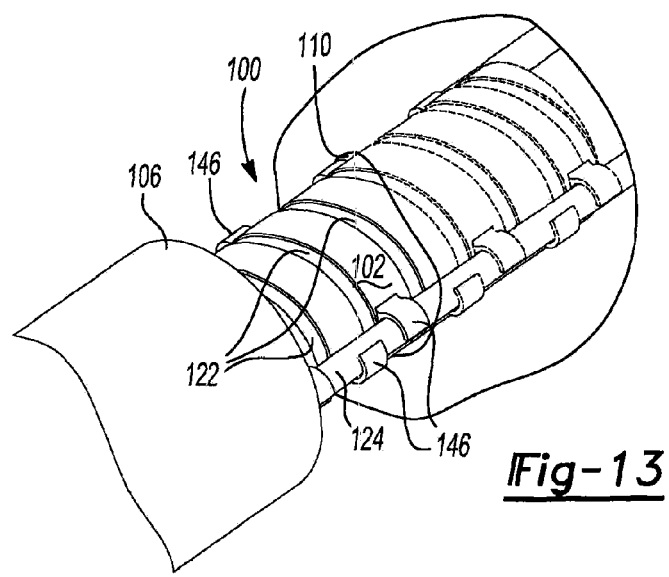
FIG. 13 is a partial perspective view of the medical device of FIG. 7 partially inserted into the incision and placed over a pair of guide wires.
Figure 14:
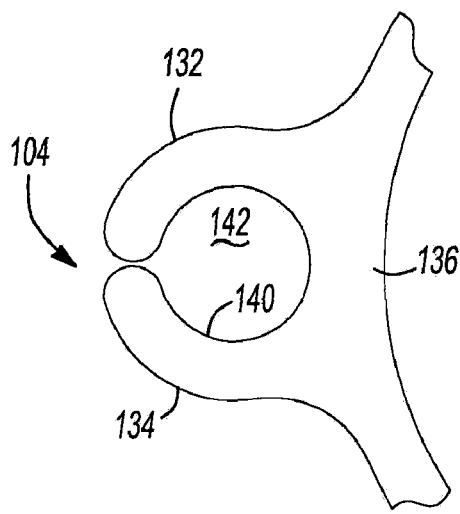
FIG. 14 is a partial front view of the guide wire holding member of FIG. 10 configured as an almost complete circle.

An optional accessory portion 106 is attached to the main cannula 102 and the guide wire holding member 104. The main cannula 102 is configured such that various medical devices (not shown) can be passed from the accessory portion 106 through the main cannula 102. A tip 108 of the main cannula 102 is configured to be inserted into a patient (not shown) through an incision 110, as depicted in FIGS. 11, 12 and 13. Various items can be passed from the accessory portion 106 through the main cannula 102 and into the patient. It will be appreciated that the various items can include but are not limited to balloon catheters, arthroscopic scopes, suction devices, or any other suitable tools to be inserted into a patient during a medical procedure.

The main cannula includes the tip 108 which is distal from a main cannula 112 connecting point that connects to the accessory portion 106. It will be appreciated that the main cannula 102 can be circular as depicted in FIG. 2, or can be configured with other shapes such as ovals or rectangular shapes as needed in various medical applications. The main cannula 102 has a tip diameter 114 and a connecting point diameter 116 both of which can be identical or vary from one another. More specifically, the connecting point diameter 116 can be smaller than the tip diameter 114 when the medical device 100 can be configured to suspend a balloon catheter (not shown) in the main cannula 102 and hold the balloon catheter within the accessory portion 106. Moreover, the length and the diameter of the main cannula 102 can be varied based on the medical application as needed.

Figure 9:
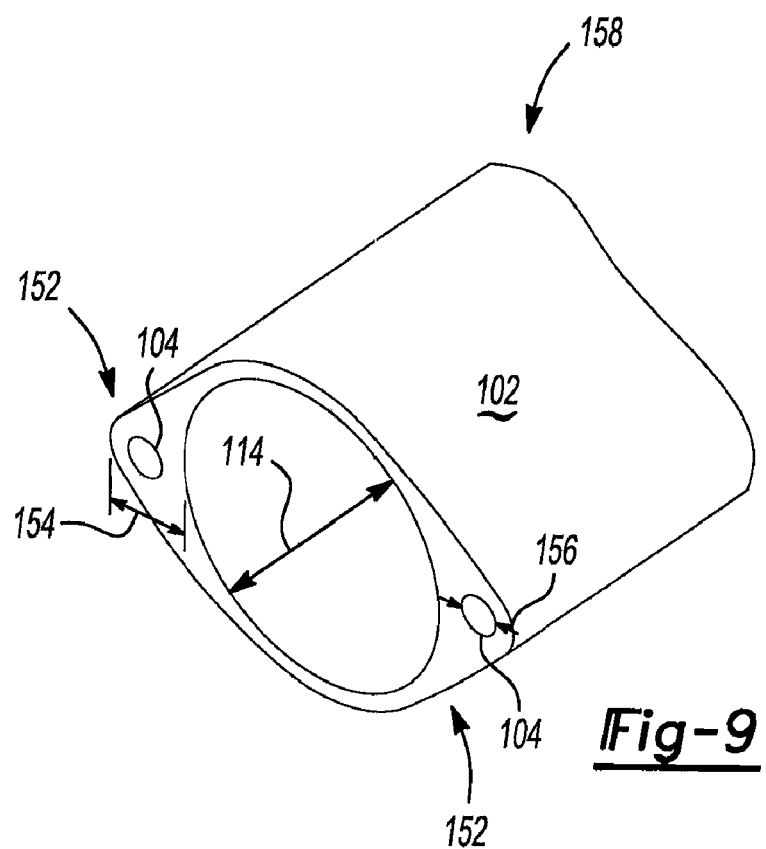
FIG. 9 is a partial perspective view showing the main cannula constructed in accordance with the various embodiments of the present invention showing the guide wire holding members contained within the walls of the main cannula.

The main cannula 102 also includes a wall thickness that is generally indicated by reference numeral 118. The wall thickness 118 of the main cannula 102 is generally the same throughout portions of the main cannula 102. Other embodiments of the present invention, however, may vary the wall thickness 118 of the main cannula 102 by, for example, using different configurations of an exterior of the main cannula 102, an example of which is shown in FIG. 9.

Figure 5:
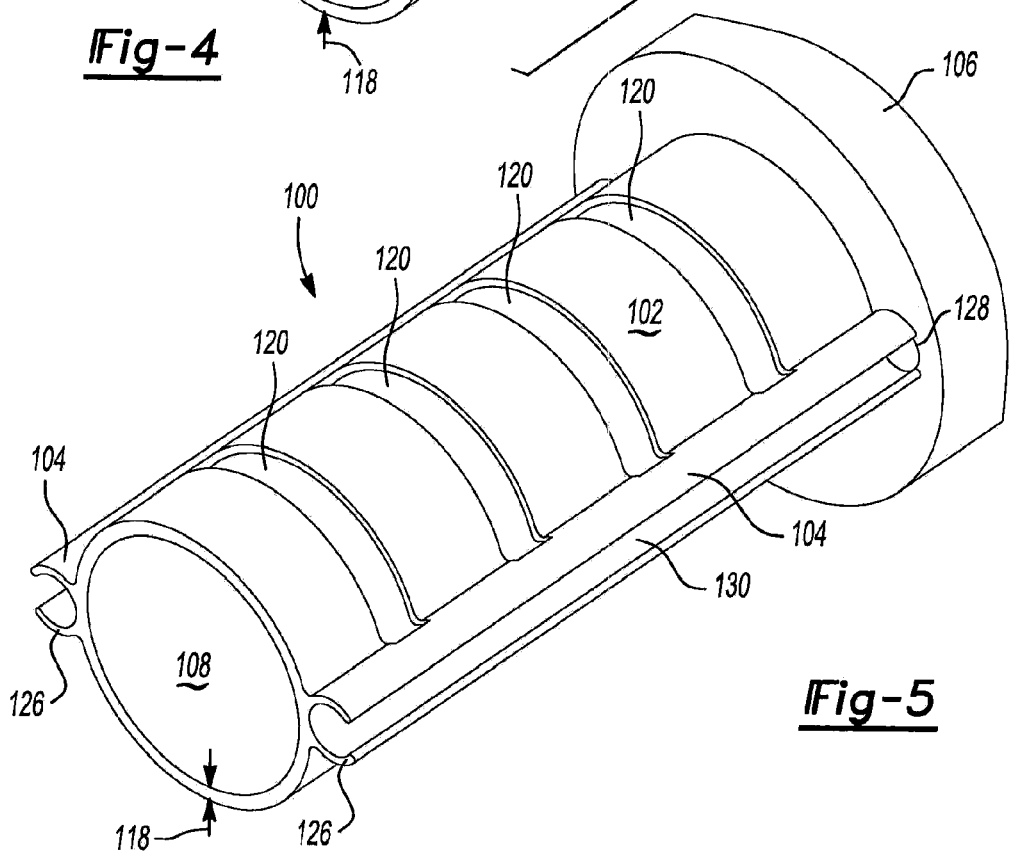
FIG. 5 is similar to FIG. 2 but shows the cannula member having graduated ring portions formed thereon.

With reference to FIG. 5, the medical device 100 may be configured with a plurality of graduated ring portions 120. The graduated ring portions 120 cover at least partially the exterior of the main cannula 102. It will be appreciated that the graduated ring portions 120 can be configured as indentations along the exterior of the main cannula 102 such that the wall thickness 118 at each of the graduated rings 120 is less than an adjacent portion of the exterior of the main cannula 102 is not contained in the graduated ring 120. It will additionally be appreciated that the graduated ring portions 120 can be configured such that the wall thickness 118 at each of the graduated rings 120 is greater than the adjacent portion of the exterior of the main cannula 102 not otherwise within one of the graduated rings 120. For example, a user (not shown) could run their hand across the exterior of the main cannula 102 and either feel indentations where the wall thickness 118 was less than—or feel raised bumps where the wall thickness 118 was greater than—the adjacent exterior of the main cannula 102 not otherwise having a graduated ring 120.

With reference to FIG. 12, it will be appreciated that the graduated rings 120 can be configured to hold the medical device 100 in the incision 110. More specifically, as the medical device 100 is inserted into the incision 110 the graduated ring portions 120 will grab and/or hold the incision 110 more securely thus making it more difficult to remove the medical device 100 from the patient.

Figure 6:
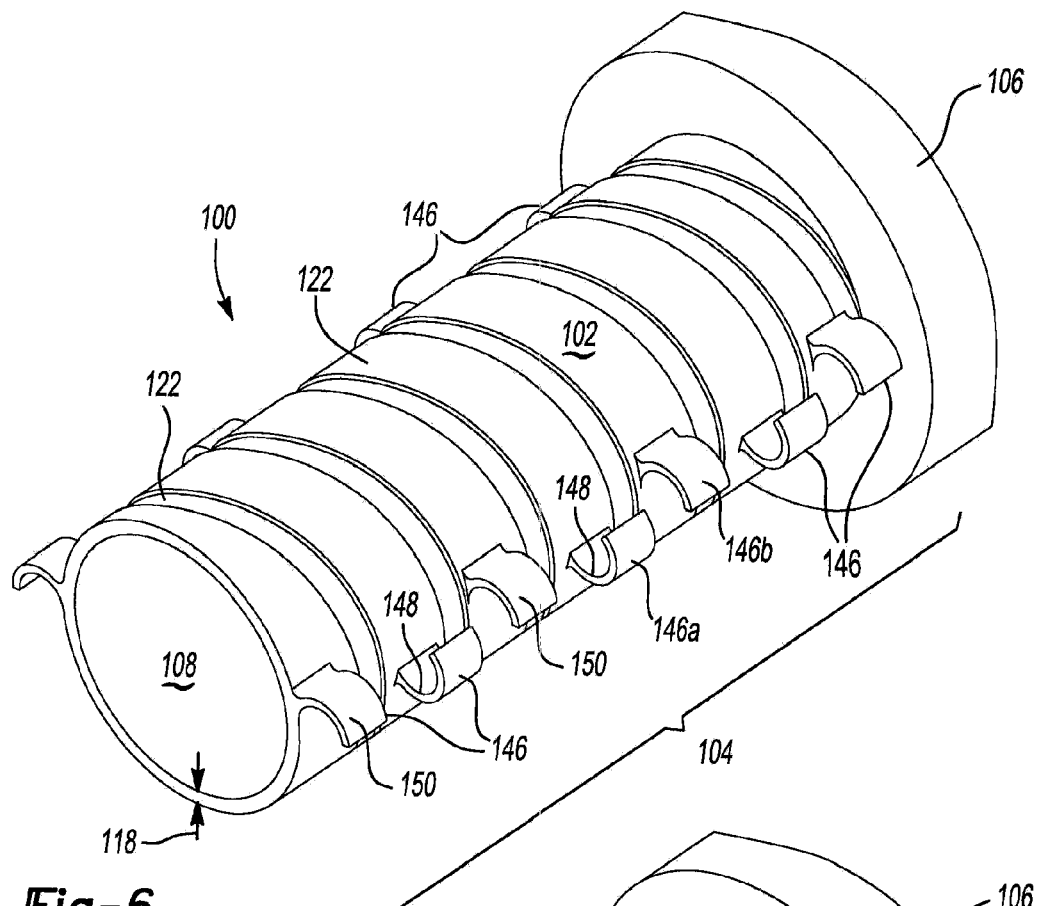
FIG. 6 is similar to FIG. 4 but shows the cannula member having threaded portions formed thereon and the guide wire holding members configured as the plurality of the curled portions.
Figure 7:
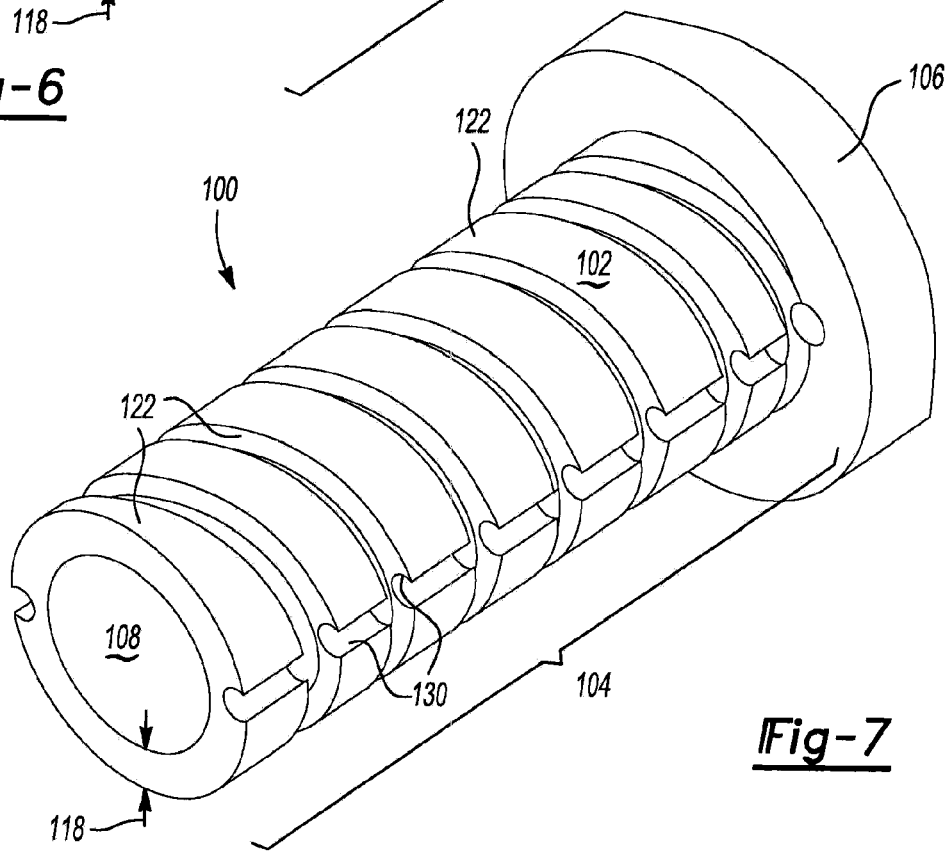
FIG. 7 is similar to FIG. 5 but shows the cannula member having the threaded portions and the guide wire holding members formed therein.

As shown in FIGS. 6 and 7, the exterior of the main cannula 102 can be configured to include threaded portions 122 over at least a portion of the exterior of the main cannula 102. The threaded portions 122 are configured to, among other things, assist in inserting the medical device 100 through the incision 110, (FIG. 13) and into the patient. The threaded portions 122 can be configured to grab the incision 110 as the medical device 100 is rotated into the patient (not shown). Moreover, the medical device 100 can be inserted into the patient and the threaded portions 122 can be configured so that depth adjustments can be easily obtained by simply rotating the medical device 100. Similar to the graduated ring portions 120, as shown in FIG. 5, the threaded portions 122 can be configured with raised portions or recessed portions having a larger wall thickness 118 or a smaller wall thickness 118 compared to the adjacent non-threaded portions 122 of the exterior of the main cannula 102 respectively. Furthermore, the medical device 100 can be configured with differing wall thickness 118 such that certain configurations of the guide wire holding members 104 may facilitate differing wall thicknesses 118.

With reference to the various Figures the guide wire holding member 104 can be configured to hold a guide wire 124. The guide wire holding member 104 can also be configured to hold fixation pins or steerable guide wires. It will be appreciated that guide wires and/or fixation pins may be inserted into and held by the guide wire holding members 104. It will be further appreciated that the guide wires can be flexible, partially rigid or completely rigid. The guide wires can also be steerable by mechanical linkage or by application of an electrical current, such as in the application of shape memory alloys like Nitinol. The thickness of the guide wires can also vary from a thin reliable wire to a rigid pin or rod. Nevertheless, the guide wire holding member 104 when connected with the guide wire 124, provides greater stability and greater control of the medical device 100 when inserted into the patient (not shown).

With specific reference to FIG. 3, the guide wire holding members 104 can also facilitate steering of the medical device 100. More specifically, the guide wires 124 can be steerable with various systems such as Nitinol wires that will change shape, thus change direction, in response to an electrical current. The guide wires 124 can also be directed with other external devices, such as a mechanical linkage, which can force the tip of the guide wire 124 to move in response to a signal and/or a force applied by various external controls. The medical device 100, therefore can be constructed of a material, such as, but not limited to, latex or other flexible medical plastics which will bend and flex in response to the controllable motion of the guide wire 124. As the guide wire 124 changes direction and otherwise navigates within the incision 110 (FIG. 11), the medical device 100 can bend and move with the guide wires 124.

As shown in various figures, a pair of guide wire holding members 104 is connected to the main cannula 102. It will be appreciated, however, a plurality of guide wire holding members 104 may be connected to the main cannula 102 such that three or more guide wire holding members 104 may be utilized. It will also be appreciated that one or more of the guide wires 124 can be inserted through one or more of the guide wire holding members 104. It will be appreciated that each of the guide wire holding members 104 may be identical or vary from one another. More specifically, the guide wire holding members 104 as depicted in FIG. 2, can be used in conjunction with the guide wire holding members 104 as depicted in FIG. 4 on the medical device 100. It will further be appreciated, therefore, while a single guide wire holding member 104 may be discussed hitherto and throughout, one or more guide wire holding members 104 may be connected to the main cannula 102 as needed such that discussion of a single guide wire holding member 104 does not limit the present invention as such.

Figure 8:
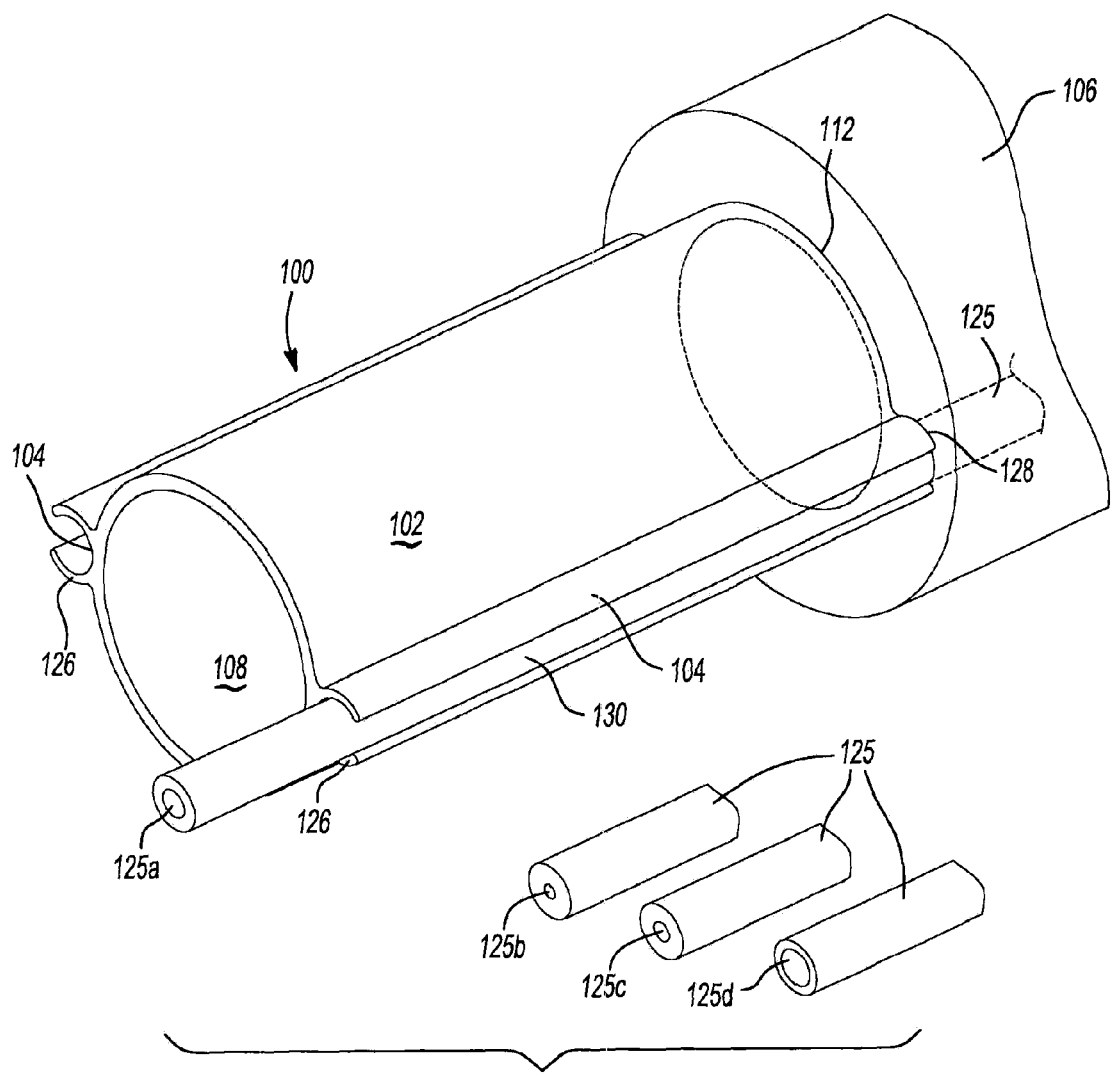
FIG. 8 is similar to FIG. 2 but shows inserts with variable inside diameters disposed within the guide wire holding members.

With reference to FIG. 2 and FIG. 5, the guide wire holding member 104 is configured as a continuous c-shaped channel. With reference to FIG. 7, the guide wire holding member is configured with c-shaped channel interrupted with the threads 122. In FIG. 8, the guide wire holding member 104 includes an insert 125 disposed therein. The insert 125 includes varying inner diameters 125A, 125B, 125C and 125D. The guide wire 124 of varying configurations can be inserted into the insert 125. As such, the guide wire holding member 124 need not be configured to accommodate varying configurations of the guide wire 124 but only the insert 125.

The insert 125, in contrast, can have fixed outer diameter while having a variable inside diameter thus providing modular functionality to accommodate various configurations or diameters of the guide wire 124.

The guide wire holding member 104 has a tip 126 on the same end as the main cannula tip 108. The guide wire holding member 104 has a guide wire holding member connecting point 128 which is distal from the guide wire holding member tip 126. As such, the guide wire holding member connection point 128 is open to the accessory portion 106 such that the guide wire 124 can be passed therethrough. The c-shaped channel of the guide wire holding member 104 can be configured as a generally circular channel such that walls 130 of the channel have about 270 degrees of material. It will be appreciated that if the walls 130 had 360 degrees of material the guide wire holding member would be configured similar to one of the pair of smaller tubes 14 as shown in FIG. 1. More specifically, the walls 130 of the guide wire holding member 104 include a first channel portion 132 and a second channel portion 134 connected to a base portion 136, all of which are connected to the main cannula 102, as shown in FIG. 10 in greater detail.

Figure 15:
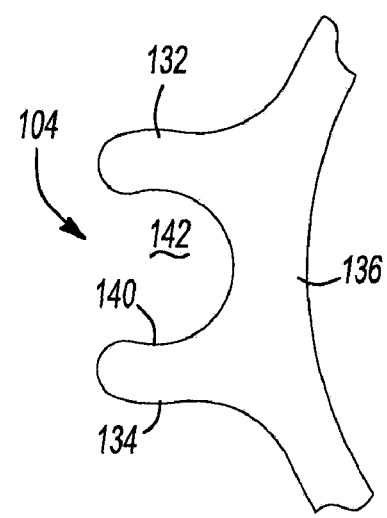
FIG. 15 is a partial front view of the guide wire holding member of FIG. 10 configured as a half circle.
Figure 16:
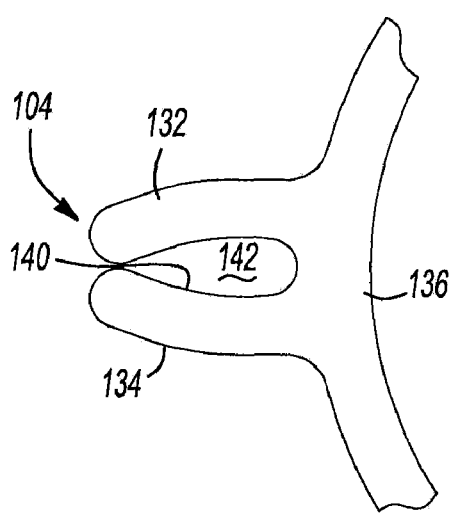
FIG. 16 is a partial front view of the guide wire holding member of FIG. 10 configured in a shape similar to a clam shell.
Figure 17:
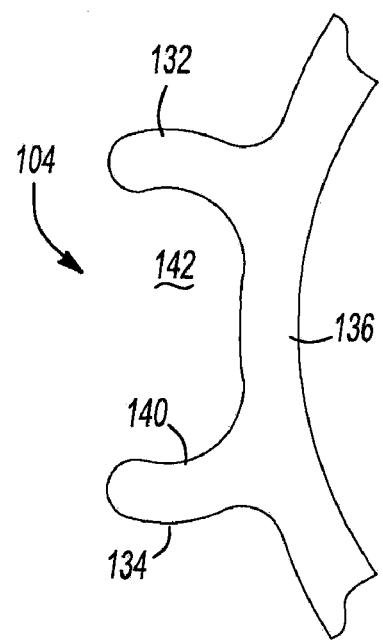
FIG. 17 is a partial front view of the guide wire holding member of FIG. 10 configured as an elongated oval shape.

In the various embodiments, the guide wire holding member 104 can be configured such that it forms an incomplete circle. For example, the material can be configured to occupy about 270 degrees. To that end, the first channel portion 132 and the second channel portion 134 can be symmetrical such that their respective arc lengths occupy about 135 degrees each. With reference to FIGS. 14, 15, 16 and 17, the arc length of the first channel portion 132 and the second channel portion 134 can also be asymmetrical. Moreover, the first channel portion 132 and the second channel portion 134 need not be continuous throughout the length of the main (cannula 102 from the main cannula tip 108 to the main cannula connecting point 112. More specifically, the first channel portion 132, the second channel portion 134, and the base portion 136 from an interior concave portion 140 that defines an interior channel 142 throughout the guide wire holding member 104. In the various embodiments, the first channel portion 132 can be spaced from the second channel portion 134 such that the interior of the first channel portion 132 the base portion 136 and the second channel portion 134 neither form a perfect nor an incomplete circle but more of an elongated space capped by the two channel portions 132, 134; as shown in FIG. 17. Furthermore, the first channel portion 132 can be spaced from the second channel portion 134 a distance smaller than that would have formed the perfect or otherwise incomplete circle. More specifically, the first channel portion 132 and the second channel portion 134 are spaced close enough where the interior channel 142 may resemble a clamshell configuration rather than an imperfect circle, as shown in FIG. 16. Additionally, the interior channel 142 can be configured as almost a complete circle (FIG. 14) or as a half-circle (FIG. 15.)

Figure 10:
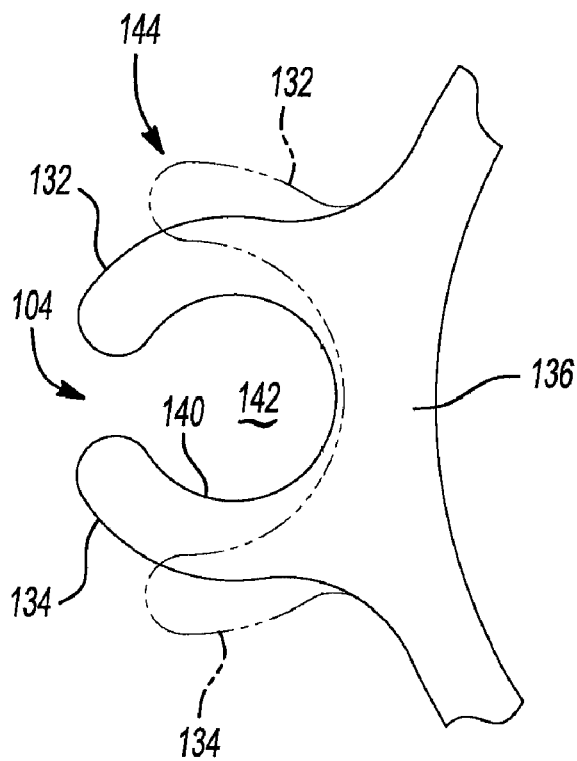
FIG. 10 is a partial front view of the guide wire holding member of FIG. 2 configured as a c-shaped channel and further showing (in shadow) the c-shaped channel in an expanded condition.

As shown in shadow in FIG. 10 the guide wire holding member 104 can be in a deflected position, generally indicated by reference numeral 144. More specifically, the guide wire holding member 104 can be constructed from a flexible material that allows the guide wire holding member 104 to be stretched. It will be appreciated that this stretching can occur when the medical device 100 is removed from the injection molding machine mold (not shown). Moreover, the guide wire holding member 104 may stretch into a deflected position 144 when the guide wire 124 is removed therefrom.

The guide wire holding members 104 are configured in a c-channel configuration to facilitate manufacturing and use of the medical device. While the guide wire holding members 104 may be configured as separate full length tubes, as shown in FIG. 1, this construction as noted above can be expensive and imprecise. As such the guide wire holding members 104 of the present invention are configured so that they can be more easily extracted from the injection mold and thus do not require the use of tapered pins with exacting alignment. By using the c-shaped guide wire holding member 104 as opposed to a long constant tube, the injection molding machine lay up mold can omit the use of the pins altogether, thus making the manufacture less costly and complex. Furthermore, the medical device 100 can be removed from the injection mold (not shown) by peeling it away or stretching it over portions of the mold as opposed to removing it from tapered pins as discussed above.

With reference to FIGS. 4 and 6, the guide wire holding member 104 is configured as a plurality of curled tabs 146. The plurality of the curled tabs 146 can be configured similar to the c-shaped channel as depicted in FIGS. 2, 5 and 7. More specifically, the curled tabs 146 can have a concave portion 148 and a convex portion 150. The plurality of the curled tabs 146 can be configured such that each of the curled tabs 146 is spaced axially along the main cannula 102 from each of the other curled tabs 146. Furthermore, each of the curled tabs 146 can be configured such that the concave portion 148 of a first curled tab 146a is facing a direction opposite from an adjacent curled tab 146b. It will be appreciated that the plurality of curled tabs 146 can be configured such that the concave portions 148 of each of the curled tabs 146 can be oriented such that the plurality of curled tabs 146 holds the guide wires 124 of various configurations.

It will be appreciated that in the various embodiments, the plurality of curled tabs 146 can be configured as about 135 degree arcs. It will also be appreciated that the arc length of material of each curled tab 146 can be less than or greater than 135 degrees of arc such that each curled tab 140 can have varying degrees of an arc length of material. It will be further appreciated that each individual curled tab 146 can otherwise be configured as generally orthogonal (not shown) from the exterior of the main cannula 102 such that each individual curled tab would not be curled but in such a relation to other tabs to secure the guide wire 124. The plurality of curled tabs 146 can also be configured to hold the guide wire 124 and not sandwich the guide wire 124 between each of the curled tabs 146. More specifically, each of the curled tabs 146 can be spaced from the adjacent curled tabs so that the guide wire 124 is held between the plurality of curled tabs 146 and not snuggly between them.

The plurality of curled tabs 146 are connected to at least a portion of the main cannula 102, but can otherwise occupy the complete length of the main cannula 102 from the main cannula tip 108 (FIG. 2) to the main cannula connecting portion 112 (FIG. 2). It will be appreciated that having curled tabs 146 along the entire length of the main cannula 102 is not required to provide suitable stability for the medical device 100 when inserted into the incision 110, as shown in FIG. 13.

With reference to FIG. 6, the exterior of the main cannula 102 is configured with threaded portions 122 throughout the length of the main cannula 102. It will be appreciated that the threaded portions 122 may intersect the guide wire holding members 104 in the spaces between the individual curled tabs 146. It will be further appreciated that the convex face 150 of the curled tabs 146 faces the direction that is required to turn and thus insert the medical device 100 into the incision 110 as shown in FIG. 10. In this situation, the concave face 148 of the curled tabs 146 faces the direction of rotation required to remove the medical device from the incision 110. Moreover, the concave portion 148 can face the direction of rotation required to extract the medical device 100, which can serve to further secure the medical device 100 in the incision 110.

The medical device 100 may be constructed of various materials suitable for use in a medial and/or a surgical arena. The medical device 100 may be formed of various metals such as but not limited to cobalt chrome or titanium which otherwise allows the user to sterilize the medical device 100 in a suitable sterilization process prior to use. Moreover, the medical device 100 may be constructed of a suitable sterile and disposable plastic that will be used for a single use and then discarded. If the medical device 100 is constructed of a single use plastic, the medical device 100 can be configured to be reduced in length as needed during the operation. More specifically, the medical device 100 can be extended or trimmed to size in situ and then inserted into the patient as needed.

The accessory portion 106 can be sized with a larger diameter as shown in the various figures. It will be appreciated, however, the accessory portion 106 is optional and can be removed altogether. Further, the accessory portion diameter can be the same or smaller than the main cannula diameter 116.

With reference to FIGS. 11, 12 and 13, the medical device 100 can be inserted into the patient by making the incision 110 in the patient and either thrusting or rotating the medical device 100 into the patient. The medical device 100 may be further stabilized by use of one or more guide wires 124 or fixation pins that are secured to the patient through the incision 110 and then connected to the medical device 100 to increase stability. The guide wire 124 may be inserted into the patient and secured in the incision 110 prior to the insertion of the medical device 100. It will be appreciated, however, the medical device 100 may be inserted into the incision 110 and the guide wire 124 subsequently can be inserted through the medical device 100 and subsequently secured to the incision 110. If the guide wires 124 are first inserted through the incision 110 and then secured to the patient, the medical device 100 is inserted into the incision 110 and connected to the guide wires 124 to increase stability. It will be appreciated that the medical device depicted in FIGS. 2 and 5 can be thrust into the incision 110 and later connected to the guide wires 124 or may be inserted over the guide wires 124 and then thrust into the incision 110. It follows that the medical device 100 depicted in FIGS. 6 and 7 may be thrust or rotated into the incision 110 and later secured to the guide wires 124.

With reference to FIG. 9, the main cannula 102 is shown with the guide wire holding members 104 connected thereto but disposed within an enlarged exterior wall of the main cannula 102 to create a smooth oval-shaped exterior contour generally indicated by reference numeral 152. It will be appreciated that a wall thickness 154 surrounding the guide wire holding members 104 is enlarged to accommodate a diameter 156 of the wire holding member. More specifically, the inner diameter (the tip diameter 114 through to the connecting point diameter 116) of the main cannula 102 remains constant, but the outer diameter is increased in asymmetrical fashion around the guide wire holding members 104 such that the exterior portion of the main cannula wraps around the guide wire holding members 104 to create the continuous oval-shaped exterior of the main cannula, as generally indicated by reference numeral 158. It will be appreciated that the threaded portions (FIG. 6) or the graduated rings (FIG. 5) may be incorporated into the exterior portions of the main cannula as shown in FIG. 6. It will also be appreciated that the wall thickness 154 need only be as thick to ensure the integrity of the walls between the guide wire holding members 104 and the main cannula 102. The wall thickness 154, therefore, may be twice the diameter of guide wire holding member 104. The wall thickness 154 may also be less or more thick depending on the material used for the main cannula 102 and the various configurations of the guide wire 124.

Figure 18:
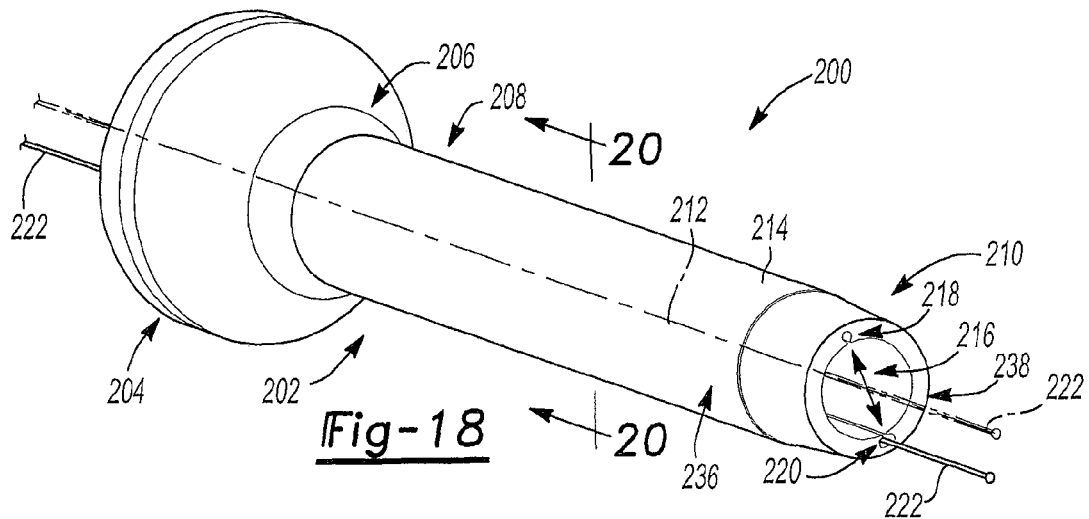
FIG. 18 is a perspective view of a cannula member having guide wire members accessible from an inner passage of the main cannula constructed in accordance with an alternative example of the present teachings.
Figure 19:
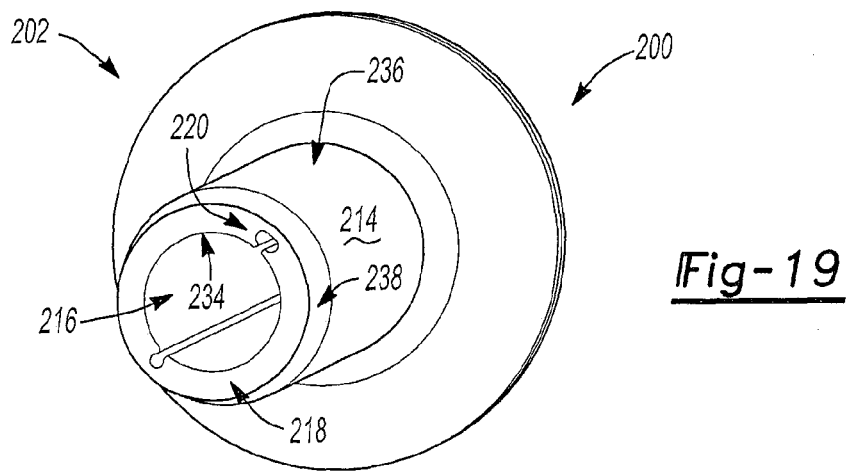
FIG. 19 is similar to FIG. 18 and shows an opposed guide wire member formed in the cylindrical wall of the cannula member.
Figure 20:
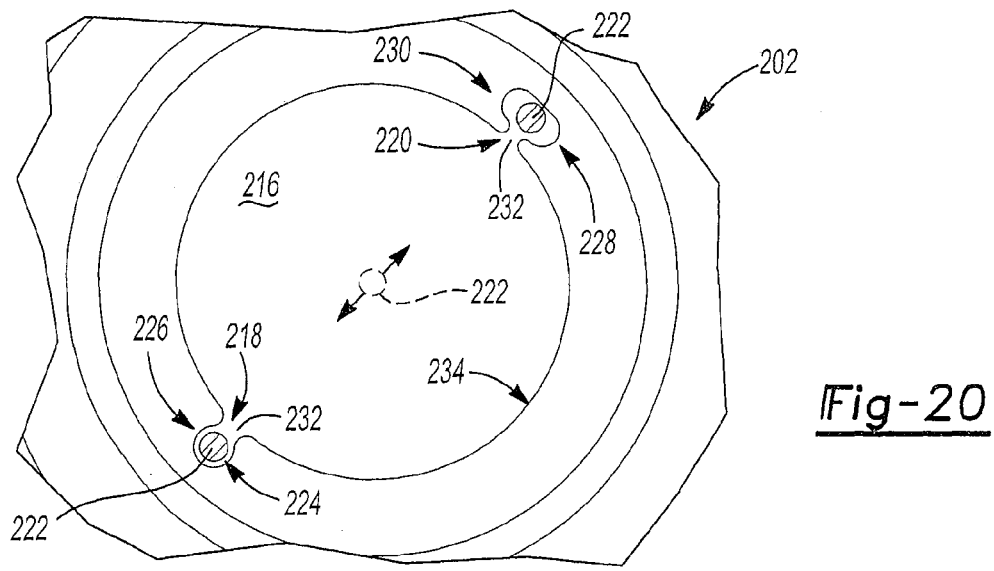
FIG. 20 is a cross-sectional view of the cannula member of FIG. 18 showing the guide members formed in the cylindrical wall accessible from the inner passage of the cannula member in accordance with the present teachings.

With reference to FIGS. 18, 19 and 20, a medical device 200 is shown that includes a cannula member 202 in accordance with various aspects of the present teachings. The cannula member 202 can define at least a first region 204, a second region 206, a third region 208 and a fourth region 210. The diameter (or width, as applicable) of the cannula member 202 at the respective regions 204, 206, 208, 210 can vary or be constant along a longitudinal axis 212 of the cannula member 202. The cannula member 202 can generally define a wall 214 throughout the regions 204, 206, 208 and 210. In the third region 208, a length of the cannula member 202 is generally greater than the length of the cannula member 202 in the first, second and fourth regions 204, 206, 210.

The wall 214 of the cannula member 202 can define an inner passage 216 that can extend along the longitudinal axis 212 and thus can extend throughout the cannula member 202. The inner passage can have a cylindrical shape, an oval shape, another suitable polygonal shape and one or more applicable combinations thereof. The inner passage 216 can continue through the first, second, third and fourth regions 204, 206, 208, 210. The wall 214 can further define a first guide wire holding member 218 and a second guide wire holding member 220 that can be formed within the wall 214 of the inner passage 216. The first guide wire holding member 218 and the second guide wire holding member 220 can be configured so that one or more of the guide wires 222 can be inserted into the first guide wire holding member 218 and the second guide wire holding member 220 from the inner passage 216. More specifically, one or more of the guide wire 222 can be placed within the inner passage 216 and can then be moved toward the guide wire holding members 218, 220 and ultimately can be placed within each of the guide wire holding members 218, 220.

The first guide wire holding member 218 can define a cavity 224 that can extend along (wholly or partially) the longitudinal axis 212 of the cannula member 202. The cavity 224 can maintain a circular cross-sectional shape 226 throughout the length of the guide wire member 218 or can vary (in shape, curvature, etc.) at applicable locations along the longitudinal axis 212. The second guide wire holding member 220 can define a cavity 228. The cavity 228 can maintain an oval cross-sectional shape 230 throughout the length of the guide wire member 220 or can vary (in shape, curvature, etc.) at applicable locations along the longitudinal axis 212.

The first guide wire holding member 218 and the second guide wire holding member 220 can each define apertures 232 that can each interrupt an inner wall surface 234 of the inner passage 216 and, as such, provide access from the inner passage 216 into the guide wire holding members 218, 220. In the example illustrated, the inner wall surface 234 of the inner passage 216 can remain generally circular but for the two apertures 232 that can interrupt the inner wall surface 234 so as to provide access to the guide wire holding members 218, 220.

In some aspects of the present teachings, the cannula member 202 can have threaded portions similar to the threaded portions 122 shown on the medical device 100, as illustrated in FIGS. 6 and 7. In addition, these threaded portions can be recessed in an outer wall surface 236 of the wall 214 of the cannula member 202. In other examples, the threaded portions can be raised relative to the outer wall surface 236 of the wall 214 of the cannula member 202. The threaded portions can also be configured as circumferential grooves similar to what is shown in FIG. 12. In further examples, one or more of the guide wires 222 can be inserted through the guide wire holding members 218, 220 and can be configured such that the cannula member 202 can be steered with pressure exerted by the guide wire 222 similar to what is shown in FIG. 3.

The first region 204 of the cannula member can have a larger diameter relative to the third region 208. As such, the inner passage 216 within the first region 204 can have a larger diameter relative to the third region 208. The second region 206 can serve as a transition to a reduced outer diameter of the third region 208 from the relatively larger diameter of the first region 204. The fourth region 210 can have a decreasing outer diameter relative to the third region 208 such that the outer diameter of the fourth region 210 of the cannula member 202 can decrease from the third region 208 to a tip 238 of the cannula member 202. At the tip 238, the guide wire holding members 218, 220 can remain accessible so as to be configured to accept the guide wire 222 at the tip 238 and not through the apertures 232 of the inner passage 216.

In an exemplary method, one or more of the guide wires 222 can be inserted into the inner passage 216 while the incision (not specifically shown) or any portion of the anatomy is being prepared to accept the cannula member 202 and the one or more guide wires 222. The guide wires 222 can be inserted into the inner passage 216 in a direction that can be generally parallel to the longitudinal axis 212 (FIG. 18). The guide wires 222 can then be moved from the inner passage 216 into the guide wire holding members 218, 220 in a direction that can be generally perpendicular to the longitudinal axis 212. One or more portions of the guide wire holding members 218, 220 can deflect, bend and/or distort so that the one or more guide wires 222 can pass through the apertures 232 and be secured in the cavities 224.

Once the guide wires 222 are removed from the guide wire holding members 218, 220 or if the guide wires 222 become loose and/or fall out of the guide wire holding members 218, 220, the guide wires 222 can simply fall into the inner passage 216 but can be otherwise contained by the cannula member 202.

While specific aspects have been described in the specification and illustrated in the drawings, it will be understood by those skilled in the art that various changes can be made and equivalents can be substituted for elements and components thereof without departing from the scope of the present teachings, as defined in the claims. Furthermore, the mixing and matching of features, elements, components and/or functions between various aspects of the present teachings are expressly contemplated herein so that one skilled in the art will appreciate from the present teachings that features, elements, components and/or functions of one aspect of the present teachings can be incorporated (wholly or partially) into another aspect, as appropriate, unless described otherwise above. Moreover, many modifications may be made to adapt a particular situation, configuration and/or material to the present teachings without departing from the essential scope thereof. Therefore, it is intended that the present teachings not be limited to the particular aspects illustrated by the drawings and described in the specification as the best mode presently contemplated for carrying out the present teachings, but that the scope of the present teachings include many aspects and examples following within the forgoing description and the appended claims.

What is claimed is:

1. A medical device for placement in an anatomy and for use with a guide wire, the medical device comprising:

a cannula member configured to be inserted into the anatomy, said cannula member having a terminal proximal end, a terminal distal end, and a wall that includes an outer wall surface and a cylindrical inner wall surface, said inner wall surface defining an inner passage that extends along a longitudinal axis of the medical device, said outer wall surface remaining circular in cross section from said terminal proximal end to said terminal distal end; and a guide wire holding member formed in said wall of said cannula member and extending continuously from said terminal proximal end to said terminal distal end of said cannula member, said guide wire holding member defining a cavity in said wall of said cannula member between said outer wall surface and said inner wall surface and wherein said inner wall surface comprises an aperture extending continuously from said terminal proximal end to said terminal distal end of said cannula member, said aperture in communication with said cavity that permits the guide wire to move between said inner passage and said cavity of said cannula member in a direction that is generally perpendicular to said longitudinal axis of the medical device when a longitudinal axis of the guide wire is generally parallel to said longitudinal axis of the medical device.

2. The medical device of claim 1, wherein said cavity has a shape that is selected from a group consisting of a partially circular-shape and a partially oval-shape.

3. The medical device of claim 1, wherein said guide wire holding member is bendable.

4. The medical device of claim 1, wherein said guide wire holding member is steerable in response to motion of the guide wire.

5. The medical device of claim 1, wherein said aperture permits the guide wire to move between said inner passage and said cavity of said cannula member at any location along said longitudinal axis of the medical device.

6. The medical device of claim 1, wherein said aperture permits the guide wire to move between said inner passage and said cavity of said cannula member without moving the guide wire in a direction along said longitudinal axis of the cannula member.

7. A medical device for placement in an anatomy and for use with a guide wire, the medical device comprising:

a cannula member configured to be inserted into the anatomy, said cannula member having a terminal proximal end, a terminal distal end, and a wall that includes an outer wall surface and a cylindrical inner wall surface, said inner wall surface defining an inner passage that extends along a longitudinal axis of the medical device; and a guide wire holding member formed in said wall of said cannula member and extending continuously from said terminal proximal end to said terminal distal end of said cannula member, said guide wire holding member defining a cavity in said wall of said cannula member between said outer wall surface and said inner wall surface, wherein said inner wall surface comprises an aperture extending continuously from said terminal proximal end to said terminal distal end of said cannula member, said aperture in communication with said cavity that permits the guide wire to move between said inner passage and said cavity of said cannula member in a direction that is generally perpendicular to said longitudinal axis of the medical device when a longitudinal axis of the guide wire is generally parallel to said longitudinal axis of the medical device, and wherein said cannula member is configured with threaded portions formed from said outer cylindrical wall of said cannula member.

8. The medical device of claim 7, wherein said threaded portions are recessed in said outer cylindrical wall of said cannula member.

9. The medical device of claim 7, wherein said threaded portions are raised relative to said outer cylindrical wall of said cannula member.

10. A medical device for placement in an anatomy and for use with one or more guide wires, the medical device comprising:

a cannula member configured to be inserted into the anatomy, said cannula member having a terminal proximal end and a terminal distal end and having a length measured from said terminal proximal end to said terminal distal end, said cannula member having a wall that includes an outer wall surface and a cylindrical inner wall surface, said inner wall surface defining an inner passage that extends along a longitudinal axis of the medical device; and a first guide wire holding member and a second guide wire holding member formed in said wall of said cannula member between said outer wall surface and said inner wall surface, said first and second guide wire holding members each defining a respective cavity in said wall of said cannula member and a respective aperture in said inner wall surface in continuous communication with said respective cavity that permits the guide wire to move between said inner passage and said respective cavity of said cannula member, wherein each of said cavities and apertures associated with said first and second guide wire holding members and said inner passage extends continuously along the length of said cannula member from said terminal proximal end to said terminal distal end.

11. The medical device of claim 10, wherein said first and second guide wire holding members are radially opposed to one another.

12. The medical device of claim 10, wherein said cavity has a shape that is selected from a group consisting of a partially circular-shape and a partially oval-shape.

13. The medical device of claim 10, wherein said apertures in said inner wall surface in continuous communication with said cavities permit the guide wire to move between said inner passage and said cavities of said cannula member in a direction that is generally perpendicular to said longitudinal axis of the medical device when a longitudinal axis of the guide is generally parallel to said longitudinal axis of the medical device.

14. A method of use for a medical device and a guide wire for placement in an anatomy, the method comprising:

providing a cannula member having a terminal proximal end, a terminal distal end, and a wall having an outer surface and a cylindrical inner surface, wherein the inner surface defines an inner passage, wherein the cannula member defines a longitudinal axis;

providing the guide wire in said inner passage, wherein the guide wire defines a longitudinal axis; and moving the guide wire through an aperture between said inner passage and a cavity formed in said wall between said inner surface and said outer surface in a direction that is generally perpendicular to said longitudinal axis of said cannula member when said longitudinal axis of the guide wire is generally parallel to said longitudinal axis of said cannula member, said cavity and said aperture each extending continuously from said terminal proximal end to said terminal distal end of said cannula member.

15. The method of claim 14, further comprising removing said guide wire from said cavity by drawing said guide wire from said cavity into said inner passage through said aperture.

16. The method of claim 14, further comprising steering said cannula member in response to motion of the guide wire.

17. The method of claim 14, wherein the guide wire is movable between said inner passage and said cavity through said aperture without moving the guide wire in a direction along said longitudinal axis of the cannula member.

18. The method of claim 14, wherein the guide wire is movable between said inner passage and said cavity through said aperture at any location along said longitudinal axis of the cannula member.

19. A medical device for placement in an anatomy and for use with a guide wire, the medical device comprising:

a cannula member configured to be inserted into the anatomy, said cannula member having a terminal proximal end, a terminal distal end, and a wall that includes an outer wall surface and an inner wall surface, said inner wall surface defining an inner passage that extends along a longitudinal axis of the medical device from said terminal proximal end to said terminal distal end, said outer wall surface having a circular cross section with an outer diameter, and said inner wall surface having a circular cross section with an inner diameter; and a guide wire holding member formed in said wall of said cannula member and extending continuously from said terminal proximal end to said terminal distal end of said cannula member, said guide wire holding member defining a cavity in said wall of said cannula member between said outer diameter of said outer wall surface and said inner diameter of said inner wall surface, and wherein said inner wall surface defines an aperture extending continuously from said terminal proximal end to said terminal distal end of said cannula member, said aperture in communication with said cavity to permit the guide wire to move between said inner passage and said cavity of said cannula member in a direction that is generally perpendicular to said longitudinal axis of the medical device when a longitudinal axis of the guide wire is generally parallel to said longitudinal axis of the medical device.

* * * * *

UNITED STATES PATENT AND TRADEMARK OFFICE
CERTIFICATE OF CORRECTION

PATENT NO. : 7,828,751 B2
APPLICATION NO. : 11/745215
DATED : November 9, 2010
INVENTOR(S) : Kevin T. Stone It is certified that error appears in the above-identified patent and that said Letters Patent is hereby corrected as shown below:

Column 2, Line 31

"embodiment" should be --embodiments--

Signed and Sealed this
Ninth Day of April, 2013

Teresa Stanek Rea
*Acting Director of the United States Patent and Trademark Office*